United States Patent [19]

Ullrich et al.

[11] Patent Number: 4,805,634
[45] Date of Patent: Feb. 21, 1989

[54] ADAPTER ASSEMBLY FOR USE WITH A CRANIAL BIOSENSOR

[75] Inventors: Georg J. Ullrich, Freiburg im Breisgau; Karl-Heinz Pomorin, Stegen; Harald Kronberg, Staufen; Günter Bramm, Mandelbachtal; Peter Koschke, Bad Feilnbach; Pavel Novak, Munich; Michael R. Gaab, Hanover, all of Fed. Rep. of Germany

[73] Assignee: Hellige GmbH, Freiburg, Fed. Rep. of Germany

[21] Appl. No.: 58,057

[22] Filed: Jun. 4, 1987

[30] Foreign Application Priority Data

Jun. 6, 1986 [EP] European Pat. Off. ........ 86107721.2

[51] Int. Cl.⁴ .............................................. A61B 5/00
[52] U.S. Cl. ..................................... 128/748; 128/345
[58] Field of Search ............... 128/748, 303 R, 303 B, 128/345; 604/93, 175

[56] References Cited

U.S. PATENT DOCUMENTS

| 4,186,728 | 2/1980 | Van Lotrineen | 128/748 X |
| 4,246,908 | 1/1981 | Inagaki et al. | 128/748 |
| 4,354,506 | 10/1982 | Sakaguchi et al. | 128/748 |
| 4,378,809 | 4/1983 | Cosman | 128/748 |
| 4,494,411 | 1/1985 | Koschke et al. | 128/748 X |
| 4,502,491 | 3/1985 | Ender et al. | 128/748 X |
| 4,572,212 | 2/1986 | Letterio | 128/748 |

FOREIGN PATENT DOCUMENTS 2720455 11/1978 Fed. Rep. of Germany ...... 128/748

Primary Examiner—Kyle L. Howell
Assistant Examiner—Angela D. Sykes
Attorney, Agent, or Firm—Edward J. Whitfield

[57] ABSTRACT

Disclosed is an adapter assembly for accurately positioning a removable biosensor implanted in the cranium or skull cap. The assembly comprises an outer sleeve member insertable into a hole bored through the skull cap and an inner sleeve member coaxial with the outer sleeve. The sleeve members are constructed so as to permit slidable insertion and removal of the biosensor and to ensure accurate, tilt-free alignment thereof, thus enabling precise, error-free measurement.

10 Claims, 3 Drawing Sheets

ADAPTER ASSEMBLY FOR USE WITH A CRANIAL BIOSENSOR

FIELD OF THE INVENTION

This invention relates to an adapter assembly for accurately positioning a removable biosensor implanted in the cranium or skull cap.

BACKGROUND OF THE INVENTION

In order to enable the pressure in the interior of the skull to be measured, it has hitherto been customary to drill a hole of about 11 mm diameter in the skull bone and to cut a thread, in order to enable a pressure sensor to be adjusted at the correct depth and with the measurement membrane aligned coplanar to the dura mater (hard meninx, hereinafter called "dura"). For this purpose, a precise remeasurement of the depth to which the thread can be cut is necessary. When the thread itself is cut and also when the sensor is screw-adjusted, relatively large, especially radial forces act, and this causes the bone material to recede. The consequence is that, even if an adapter sleeve inserted into the bone by means of the thread is used, the entire measurement system starts to wobble after some time. It must then be readjusted again and again in order to meet the absolute requirement of an accurate measurement, namely, the coplanar-epidural alignment of the measurement membrane.

A further problem in the hitherto usual methods for measuring the pressure in the interior of the skull results from the extensive sticking of the adapter sleeves in the bone. When the adapter sleeves have to be removed again after a measurement period, it happens to quite frequently that a part of the bone is broken or torn out. Moreover, it is found in practice that cutting the thread in the skull bone for insertion of the adapter sleeve demands extensive experience of the brain surgeon. In spite of extensive experience, problems arise again and again due to tilting of the measuring sensor.

An improvement over the screwed-in adapter sleeve is described in published European patent application No. 0074037. According to EPA No. 74037, after the scalp has been cut open, a hole with defined steps is first drilled in the skull bone by means of a stepped trephine, into which hold the adapter sleeve is inserted, which sleeve is in the form of a flexible tubular member provided with outward-expanding flexible tongues and, in the upper region, has a widened section which protrudes outwards like a flange and is meant to ensure, by interaction with the stepping in the drilled table, the correct reference depth for the insertion of the pressure sensor. The adapter sleeve of EPA No. 74037 is provided at the lower end of the flexible tongues with external engagement cams which, with the adapter sleeve inserted, engage below the lower edge of the hole in the skull bone and thus fix the adapter sleeve in position. In order to adjust the reference depth, an intermediate ring can be slipped over the adapter sleeve from the free ends of the flexible tongues, which ring rests on the shoulder in the bore when the adapter sleeve has been inserted into the hole in the skull bone. Although reproducible stepped bores can generally be made with surgical stepped trephines, clinical tests have shown that the step height can nevertheless vary. For example, at a mean step height of 2.6 mm, variations between 1.7 mm and 3.8 mm step height were found. Since, however, the membrane of the pressure sensor must be adjusted to a precisely defined depth position, the variations in the step height are compensated in the adapter assembly of EPA 74037 by means of variously sized intermediate rings.

According to EPA No. 74037, the pressure sensor is screwed into the adapter sleeve which is provided for this purpose with an internal thread in its upper region. A certain depth adjustment is also achievable via this thread. In addition, the internal thread in the upper region of the expanding sleeve serves for anchoring an insertion and replacement tool. However, injuries on removal or replacement of the sensor are possible even with the adapter of EPA No. 74037, especially after a prolonged measurement time, since, as mentioned therein, sticking can occur in the lower region of the adapter sleeve and this inevitably causes injuries when the adapter sleeve is pulled out, even though these injuries are less serious than in the case where the adapter sleeve is screwed into the skull bone.

A particular problem associated with the pressure sensor adapter assembly, according to EPA No. 74037, is due to the fact that the flexible tongues of the adapter sleeve, initially only loosely inserted into the stepped bore in the skull bone, are not forced axially outwards, so that the engagement cams at the lower ends of the flexible tongues cannot engage below the lower peripheral edge of the drilled hole, until the pressure sensor is inserted into the adapter sleeve. It is then unavoidable that a certain pressure is transmitted to the measurement membrane of the sensor, particularly in the edge region thereof. This is the case especially if the pressure sensor is inserted even with only a slight tilt into the adapter sleeve. For an accurate pressure measurement at the dura, it is absolutely necessary, however, that no other pressure forces whatsoever act on the measurement membrane of the pressure sensor.

Another problem associated with the pressure sensor adapter assembly of EPA 74307 arises from the fact that the reference depth also is reproducible only in a relatively complicated or inaccurate manner. Because of the holding and adjusting thread used in the adapter sleeve, the sensor must also be constructed with relatively sharp edges and must be rotated on insertion, which, in turn involves the risk of uncontrollable pressure forces acting on the underside, that is to say in the region of the membrane edge, so that the measured result can be inaccurate. Even though EPA No. 74307 suggests the use of a bayonet closure as an alternative, this has the consequence that adjusting means of another type must then be used. Tests carried out over a prolonged period have shown that, when a bayonet closure is used, it is absolutely necessary to check repeatedly whether the closure has adequately snapped in. The feared tilting, already mentioned, can then again easily lead to inaccuracies in the measured result. By contrast, if the expanding sleeve is held loosely, it happens quite frequently that the sleeve is seated too loosely and also turns, instead of the sensor really snapping into the bayonet closure.

OBJECTS OF THE INVENTION

It is an object of the invention to provide an improved adapter assembly for accurately positioning a biosensor in the cranium or skull cap so that the pressure sensor can be slidably inserted and replaced via the adapter assembly to minimize uncontrollable additional forces acting on the measurement surface membrane, to permit accurate adjustment and alignment of the biosensor coplanar to the dura, to permit precisely reproducible reference depth, and to minimize the possibility of further injuries to the cranial bone tissue.

SUMMARY OF THE INVENTION

This invention provides an improved adapter assembly for accurately positioning a removable biosensor, having a cylindrical body portion, in a stepped circular hole bored through the cranium, the upper portion of said hole having a larger diameter than and coaxial with the lower portion so as to form a radial bearing surface intermediate said upper and lower portion, said adapter assembly comprising: (a) a first tubular member adapted for insertion into said hole, the upper portion of which tubular member is formed as a radially extending flange adapted to the inside diameter of the upper portion of the hole, the lower portion of which tubular member formed as a plurality of downwardly depending spring-like legs adapted to the inside diameter of the lower portion of the hole, the lower tips of said legs formed as outwardly extending cams; and (b) a second tubular member adapted for insertion into the first tubular member, the upper portion of which is formed as a radially outwardly extending flange adapted to the inside diameter of the upper portion of the first tubular member, the lower portion of which is adapted to the inside diameter of the lower portion of the first tubular member, the inside diameter of the second tubular member being slightly larger than the outside diameter of the biosensor such that the biosensor is slidable therein, whereby when the second tubular member is inserted into and coaxially aligned with the first tubular member the spring-like legs are urged into contact with the cranial wall defined by the lower portion of the hole and the outwardly extending cams engage the lower outer periphery of the cranium defined by the lower portion of the hole.

In accordance with the assembly of this invention, no uncontrollable additional pressure forces arise in the region of the peripheral lower edge of the sensor, that is to say in the region of the membrane. The sensor does not have to be screwed in or secured by a bayonet closure. Simple pushing into the applicator assembly suffices. The correct reference depth is automatically adjusted by insertion of the two sleeves, with the consequence that the sensor membrane will be coplanar to the dura.

BRIEF DESCRIPTION OF THE DRAWINGS

The invention is depicted in an illustrative embodiment, with reference to the drawings wherein.

DESCRIPTION OF THE PREFERRED EMBODIMENT

Figure 1:
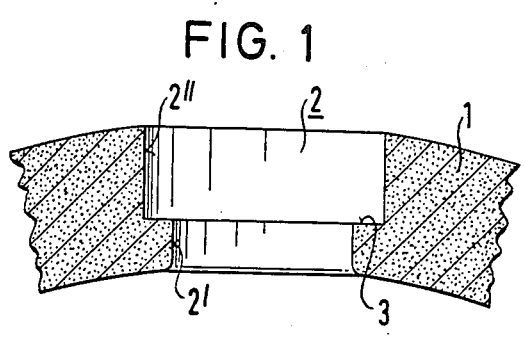
FIG. 1 shows a section of the cranial or skull bone, in which a stepped hole has been bored, for example, by means of a stepped trephine.

FIG. 1 illustrates the initial situation before the adapter assembly according to the invention is inserted. By means of a known stepped trephine, the surgeon has already made in the cranium or skull bone 1, a stepped cylindrical hole 2, having a lower narrow diameter region 2' located proximate to the dura and having a larger upper diameter 2". A radial bearing surface intermediate said upper and lower portions is indicated at 3.

Figure 2:
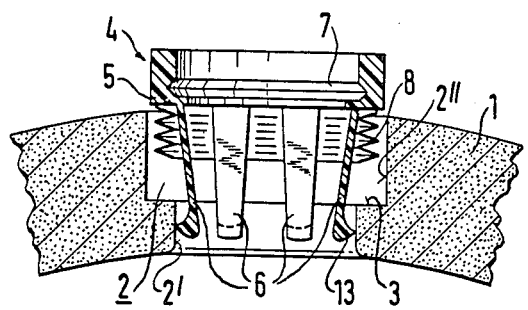
FIG. 2 shows the insertion of the spring leg sleeve into the hole.

As FIG. 2 shows, a first tubular member or sleeve 4 having a plurality of spring-like legs 6 in a radially inward-inclined position is first inserted into the hole 2. The spring-like legs 6 have outwardly extending engagement cams 13 at their lower ends. The radial pretension or inclination of the spring-like legs 6 is such that the tubular member 4 can be inserted without difficulty into the lower portion of the hole 2'. The upper portion of tubular member 4 is formed as a flange 5 radially outwardly directed, having a diameter adapted to the diameter 2" in the upper portion of the hole 2. A spring washer element 8 in the form of a rubber ring (of silicone rubber, neoprene or the like) is, in a preferred embodiment, slipped over the lower portion of sleeve 4 and bears against the lower periphery of the flange 5 in the spring leg sleeve 4 and the upper periphery of radial bearing surface 3. In addition, the sleeve 4 has, in the region of the flange 5, a peripheral inner groove 7 which serves for holding a conventional gripping tool (not shown) for insertion and removal of the sleeve 4.

Figure 3:
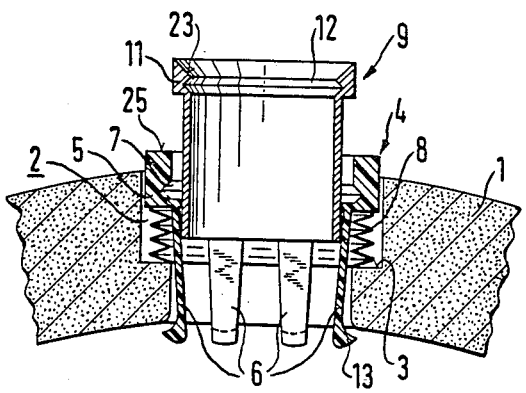
FIG. 3 shows the insertion of the expansible sleeve into the spring leg sleeve.

When the sleeve 4 has been fully inserted into the hole 2, as shown in FIG. 3, so that spring element 8 bears against the surface 3 such that the engagement cams 13 are just below the lower inner peripheral edge of the drill hole 2, a relatively thin-walled tubular member or sleeve 9 is then inserted into the sleeve 4, thus urging the spring-like legs 6 radially outwards, so that the engagement cams 13 engage the cranial bone below the peripheral lower inner edge of the hole 2 and thus fix the sleeve 4 in the correct position. In its upper (outer) region, the expanding sleeve 9 has an axial widening or flange element 11 which is adapted to the internal bore of the flange element 5 in the sleeve 4. In this widened diameter region, the sleeve 9 may likewise be provided with a peripheral internal groove 12 for gripping by means of a conventional insertion or removal tool.

Figure 4:
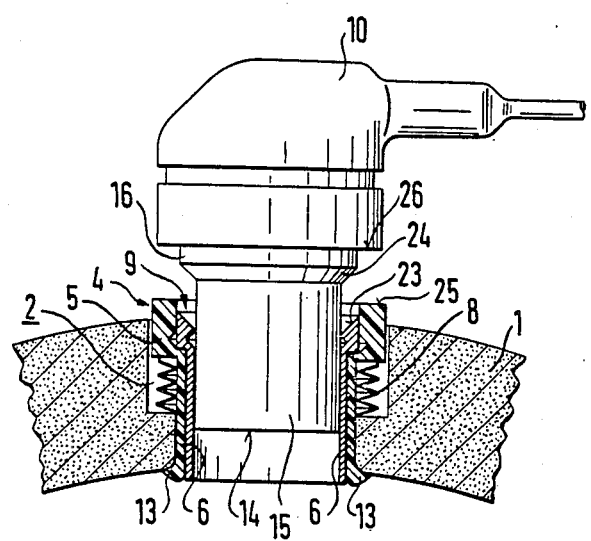
FIG. 4 shows the insertion of the measurement sensor into the expansible sleeve.

FIG. 4 illustrates the adapter assembly according to the invention, inserted fully into the hole 2 wherein the sleeve 4 and sleeve 9 and spring element 8 ensure depth compensation for any variations in the stepped drill hole 2. FIG. 4 shows how a sensor, in particular a pressure sensor 10, with a cylindrical body portion 15 is inserted into the sleeve 9 without problems and without tilt, the measurement surface membrane 14 on the underside of the pressure sensor 10 not being subjected to any uncontrolled or undesired additional pressure forces but measuring only the pressure forces emanating from the interior of the skull via the dura. Correct depth adjustment is ensured by the fact that both the top surface 23 of sleeve 9 and a stepped fitting surface 24 on the measurement sensor 10 are provided with mutually adapted chamfers. Moreover, the upper peripheral surface 25 of the sleeve 4 and also a peripheral stepped support surface 26 on the measurement sensor 10 are mutually adapted so that, with the surfaces 25, 26 abutting and the chamfered surfaces 23 and 24 abutting, a precisely reproducible insertion depth of the measurement sensor 10 with respect to the insertion depth of both the sleeve 4 and the sleeve 9 is ensured. As can be seen, the measurement sensor 10 can thus be inserted and removed without problems. Screwing-in or snapping-in by means of a bayonet closure and all the problems associated therewith, as explained above, are eliminated.

A very important point for an accurate measured result is that the pressure sensor 10, on insertion into the adapter assembly, does not expand the spring-like legs 6 of the sleeve 4 apart from one another since this has already been accomplished by the expanding sleeve 9. The pressure sensor 10 is thus protected from undesired radial forces, especially in the lower edge region of the measurement membrane 14.

The sleeve 4 can be made of suitable plastic, e.g., a plastic injection-moulding. Tests have shown that, when a plastic sleeve 4 is used, an advantageous ratio between the axial advancing force on insertion of the sleeve 9 relative to the friction of the spring-like legs 6 on the drill hole wall 2' is obtained. Thus, spring-like leg sleeves of plastic are able to compensate greater step tolerances than metallic spring-like leg sleeves. A similar advantageous effect is obtained when, in the case of using a suitable metal or metal alloy for the spring-like leg sleeve, at least the spring-like legs 6 are coated with plastic, for example, polytetraflouroethylene available under the trademark, Teflon ®. Sleeve 9 may also be made of suitable plastic but is preferably made from thin metal or metal alloy, e.g., stainless steel or titanium.

An essential advantage of the invention results from the fact that since the internal diameter of the sleeve 9 is slightly greater than the external diameter of the pressure sensor 10 in the region of the cylindrical body portion 15, when the pressure sensor 10 is slidably inserted into sleeve 9, it is not subjected to any additional undesired pressure action, especially in the region of its lower peripheral edge, that is to say in the region of the measurement surface membrane 14, and not even if the thin-walled expanding sleeve 9 is slightly deformed as a result of the spring-like legs 6 being forced apart. On the other hand, a precise reference depth on insertion of the pressure sensor into the dual sleeve arrangement 4, 9 is ensured by interaction of the chamfered surface 23 on the sleeve 9 and the chamfered surface 24 on the pressure sensor 10, whereas the axial guiding and fixing of the pressure sensor 10 in the dual sleeve arrangement 4, 9 is achieved by the mating surface 16 on the pressure sensor 10 in interaction with the peripheral inner edge of the flange 5 on the expanding sleeve. This axial guiding and fixing of the measurement sensor 10 can also be ensured by one or more grooves in the flange 5 in interaction with correspondingly adapted projections or webs instead of or in the region of the mating surface 16. A bayonet closure or the like is not necessary.

Figure 5:
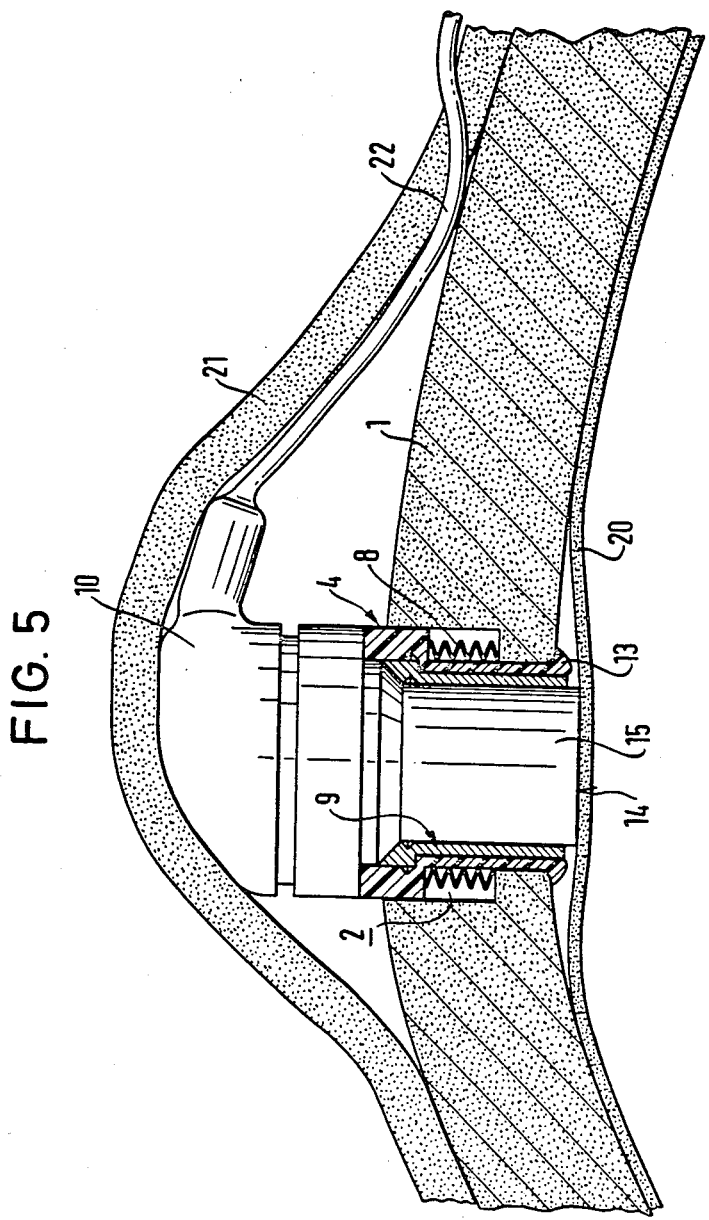
FIG. 5 shows the completed assembly.

FIG. 5 shows an assembled device for actual practice, using the adapter assembly according to the invention. The surgeon has cut open the scalp 21, made the stepped bore 2 by means of a stepped trephine and then inserted sleeve 4 provided with the spring element 8 and subsequently sleeve 9, into which the pressure sensor 10 is inserted. After fitting a bushing for the lead cable 22, the complete array is covered by the scalp 21.

Tests have shown that, with the adapter assembly according to the invention, pressure sensors for measuring the internal pressure in the skull can be used with substantially greater ease than hitherto, coupled with excellent reproducibility and reliability of the measured results. Handling and especially replacement of the biosensor (pressure sensor) can be carried out in a simple manner. The telescopic function of the ring-like spring element 8 on the spring leg sleeve 4 compensates any remaining tolerances in the step height without any problems.

If other biosensors such as, for example, transdural or even subdural $pO_2$ or $pCO_2$ sensors with a corresponding external housing shape are used, these can also be applied to the skull in a simple and reproducible manner. Corresponding comments apply to metabolism sensors, by means of which the metabolism in the upper subarachnoid space can be measured, after the dura has been opened. In the same way, sensors for the temperature and other measured variables can be applied in a simple manner by means of the adapter assembly according to the invention.

We claim:

1. An adapter assembly for accurately positioning a removable biosensor, having a cylindrical body portion, in a stepped circular hole bored through the cranium, said hole having an upper portion and a lower portion, the upper portion of said hole having a larger diameter than and coaxial with the lower portion so as to form a radial bearing surface intermediate said upper and lower portions, said adapter assembly comprising: (a) a first tubular member adapted for insertion into said hole, said tubular member having an upper portion and a lower portion, the upper portion of which tubular member is formed as a radially outwardly extending flange adapted to the inside diameter of the upper portion of the hole, the lower portion of which tubular member formed as a plurality of downwardly depending spring-like legs adapted to the inside diameter of the lower portion of the hole, said legs having lower tips formed as outwardly extending cams; and (b) a second tubular member adapted for insertion into the first tubular member, said tubular member having an upper portion and a lower portion, the upper portion of which tubular member is formed as a radially outwardly extending flange adapted to the inside diameter of the upper portion of the first tubular member, the lower portion of which is adapted to the inside diameter of the lower portion of the first tubular member, the inside diameter of the second tubular member being slightly larger than the outside diameter of the cylindrical body portion of the biosensor such that said body portion is slidable therein, whereby when the second tubular member is inserted into and coaxially aligned with the first tubular member the spring-like legs are urged into contact with the cranial wall defined by the lower portion of the hole and the outwardly extending cams engage the lower outer periphery of the cranium defined by the lower portion of the hole.

2. The adapter assembly of claim 1 including a spring washer element disposed about the lower portion of the first tubular member such that when said tubular member is inserted into the stepped hole in the cranium, the upper end of the spring washer element bears against the underside of the radially extending flange and the lower end of the spring washer element bears on the radial surface intermediate the upper and lower portions of the hole.

3. The adapter assembly of claim 2 wherein the spring washer element is made of silicone rubber.

4. The adapter assembly of claim 1 wherein the upper, inner periphery of the radially extending flange of the second tubular member has a chamfered surface such that when the body portion of the biosensor is inserted therein, said chamfered surface engages a mating radially outwardly extending chamfered surface on the body portion of the biosensor.

5. The adapter assembly of claim 1 wherein the upper surface of the radially extending flange of the first tubular member engages the lower surface of a radially outwardly extending flange on the body portion of the biosensor when the body portion is inserted into the second tubular member.

6. The adapter assembly of claim 1 wherein each of the tubular members is provided with means for engaging a functionally adapted tool whereby the tubular members are inserted into and removed from the hole in the cranium.

7. The adapter assembly of claim 6 wherein said engagement means is a peripheral groove formed in the inner surface of the radially outwardly extending flange of each tubular member.

8. The adapter assembly of claim 1 wherein the tubular members are made of plastic material or a corrosion resistant metal or metal alloy.

9. The adapter assembly of claim 8 wherein the first tubular member is made of metal or metal alloy and is coated with a plastic material, at least in the region of the spring-like legs.

10. The adapter assembly of claim 8 wherein the second tubular member is made of metal or metal alloy.

* * * * *